US005501113A

United States Patent [19]
Harrison et al.

[11] Patent Number: 5,501,113
[45] Date of Patent: Mar. 26, 1996

[54] PARTICLE MEASURING SYSTEM WITH SONICALLY MEASURED FLOW RATE

[75] Inventors: Charles Harrison, Adelphi; Zhi X. Peng, Kensington; Gladys V. Range, Silver Spring; Gary L. Morgan, Elkridge, all of Md.

[73] Assignee: Pacific Scientific Company, Newport Beach, Calif.

[21] Appl. No.: 455,400

[22] Filed: May 31, 1995

Related U.S. Application Data

[63] Continuation of Ser. No. 148,616, Nov. 8, 1993, abandoned.

[51] Int. Cl.$^6$ ............................................. G01N 15/02
[52] U.S. Cl. ............................................. 73/865.5
[58] Field of Search ........................... 73/865.5, 861.25, 73/290 V; 356/335, 336; 324/71.4

[56] References Cited

U.S. PATENT DOCUMENTS

| | | |
|---|---|---|
| 3,100,885 | 8/1963 | Welkowitz et al. . |
| 3,985,030 | 10/1976 | Charlton . |
| 4,455,870 | 6/1984 | Jorritsma . |
| 4,992,998 | 2/1991 | Woodward . |
| 5,119,676 | 6/1992 | Bower et al. . |
| 5,131,271 | 7/1992 | Haynes et al. . |
| 5,198,989 | 3/1993 | Petroff ................................. 73/861.25 |
| 5,351,118 | 9/1994 | Spinell ................................... 356/335 |

FOREIGN PATENT DOCUMENTS 1696968  12/1991  U.S.S.R. ............................... 73/865.5

OTHER PUBLICATIONS

Translation of SU 1696968, pp. 1–4.

Primary Examiner—Hezron E. Williams
Assistant Examiner—Nashmiya Ashraf
Attorney, Agent, or Firm—Lane, Aitken & McCann

[57] ABSTRACT

In a particle measuring system, a burette is provided to enable the rate of flow to a particle sensor of the particle measuring system to be continuously monitored and controlled. The burette has a central chamber and an outer chamber from which the central chamber can overflow. The central chamber of the burette is connected with the flow sample and the rate of flow through the particle sensor is measured by measuring the rate of displacement of the surface of the liquid sample in the central chamber. The rate of sonic transmission through the sample is measured by reflecting pulses from the surface of the sample at the time the central chamber overflows.

11 Claims, 2 Drawing Sheets

PARTICLE MEASURING SYSTEM WITH SONICALLY MEASURED FLOW RATE

This application is a continuation of prior complete patent application Ser. No. 08/148,616, filed Nov. 8, 1993, now abandoned.

BACKGROUND OF THE INVENTION

This invention relates to an instrument for detecting and measuring the size of particles entrained in liquid chemicals which may have variable viscosities and which may be highly corrosive and more particularly to such an instrument with an improved system for controlling the rate of liquid flow through the particle sensor of the instrument.

In particle measuring instruments for measuring particles entrained in liquids, it is important to maintain a relatively constant rate of flow through the particle sensor of the instrument for different viscosities to achieve accurate and consistent measurement of particle sizes. It is also important to know the amount of the sample that has passed through the particle sensor during a given measurement so that the density of the particles of different sizes can be determined. One method of measuring and controlling the flow rate is to cause the sample to flow into a central chamber of a burette and detecting when the sample overflows the central chamber. The time interval required to fill the central chamber gives a rough measurement of velocity and, by trial and error, the flow rate of the sample can be controlled to be an approximation of the desired rate. The problem with the above described system is that the desired flow rate has to be arrived at by trial and error through several trial runs of filling the central chamber and readjusting the flow rate after each run until the desired flow rate is achieved.

The present invention enables the flow rate to be continuously measured as the sample is passing through the particle sensor enabling the operator to instantaneously control the rate for the given sample. In addition, the system provides an accurate determination of the volume that flows through the sensor so that an accurate measurement of particle density will be obtained.

SUMMARY OF THE INVENTION

In the system of the invention, a burette with a central chamber is provided and a sonic pulse transmitter and sensor is employed to transmit sonic pulses through the sample in the central chamber to measure the position of the surface of the sample in the central chamber as the sample is caused to flow from this central chamber through a particle sensor. By repeatedly making this measurement every ½th of a second, the rate of the flow of the sample can be continuously measured from the rate of displacement of the sample surface. The rate of flow can be readily adjusted to a desired value by observing the measured rate of flow. The volume of the sample is determined by summing the increments of flow between each incremental measurement of surface position.

In accordance with the invention, the central chamber is first filled with the sample to clean out the central chamber. When the central chamber fills, it overflows and the time that the sample overflows from the central chamber is detected. At this point, the distance of the sample to the surface is measured to provide a measurement of the rate of sound travel through the sample being measured.

A tube extends from the particle sensor down into the center of the central chamber to near the bottom thereof. When the central chamber has been filled as detected by the overflow sensor, the burette is pressurized to force the sample in the central chamber up through the tube leading to the particle sensor and, at this time, the rate of flow is controlled in the manner described above. Because a measurement of the time of travel of sonic pulses passing through the sample is made at the time that the sample overflows, an accurate measurement of the rate of the sample flow is determined even though different samples have different rates of sonic transmission.

BRIEF DESCRIPTION OF THE PREFERRED EMBODIMENTS

Figure 1:
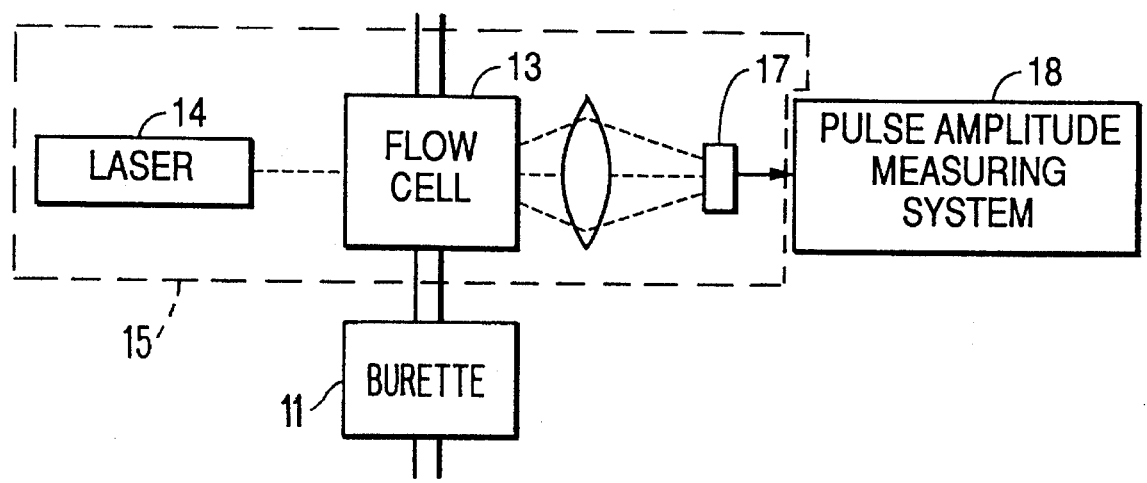
FIG. 1 schematically illustrates the particle measuring instrument of the present invention.

As shown in FIG. 1, the liquid chemical to be measured is first introduced into burette 11 and from the burette 11 is caused to flow through a flow cell 13. The flow cell 13 preferably is a sapphire flow cell as disclosed in copending patent application Ser. No. 07/973,383, filed Nov. 10, 1992, and now U.S. Pat. No. 5,371,585, invented by Gary Morgan et al. A laser 14 directs a light beam through the stream of the sample flowing through the flow cell 13 and light scattered from particles entrained in the liquid sample are detected by a photodetector 17. The pulses generated by the photodetector 17 are directed to a pulse measuring system 18 which measures the amplitude of the pulses as a determination of the size of the particles. The laser 14, the flow cell 13 and the photodetector 17 comprises a particle sensor 15.

Figure 2:
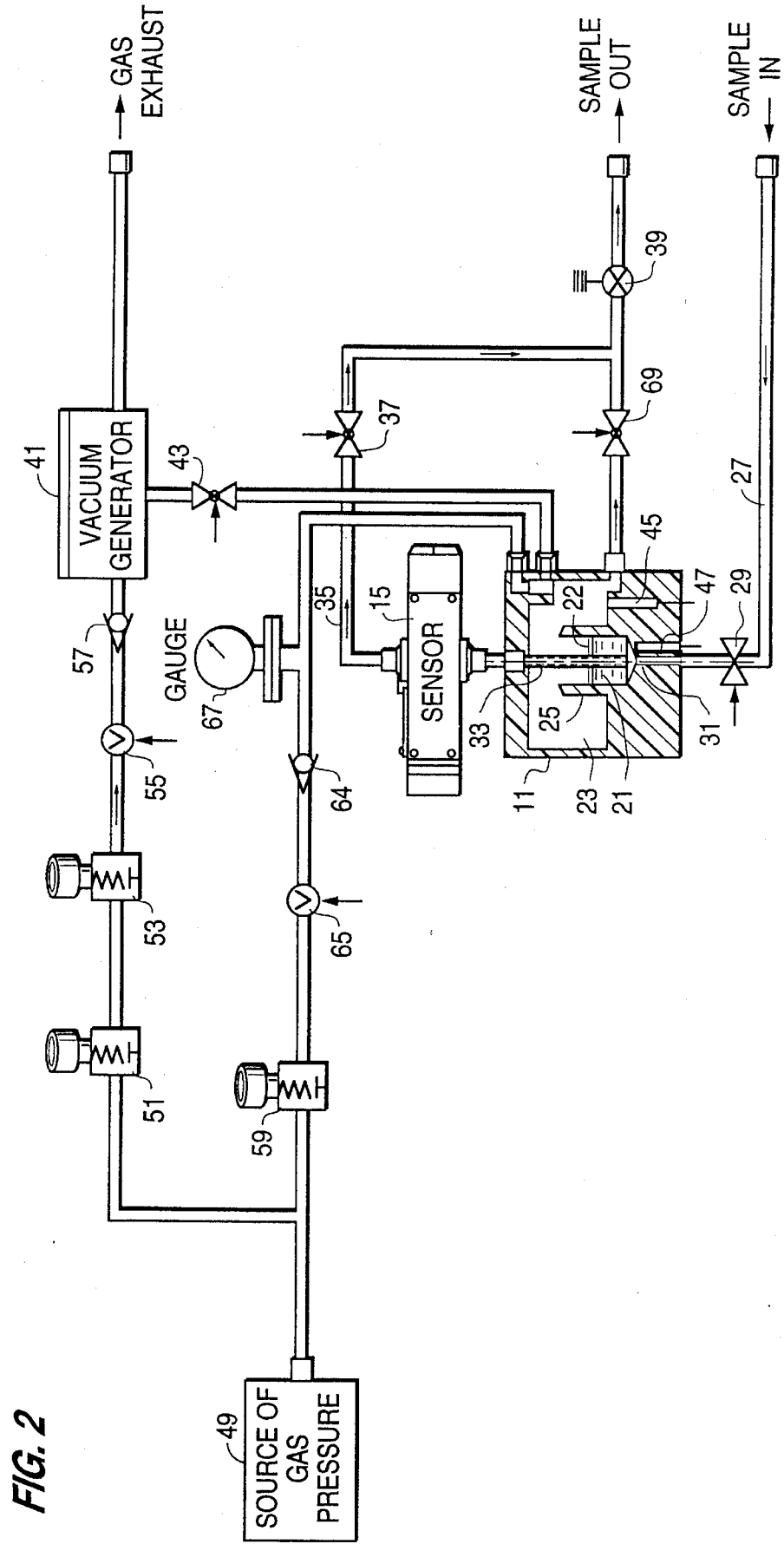
FIG. 2 schematically illustrates the flow control portion of the system of the present invention.

As shown in FIG. 2, the burette 11 has a cylindrical central chamber 21 and an outer chamber 23 separated by a cylindrical wall 25. The central chamber 21 is open at the top to the outer chamber 23 so that liquid can flow from the central chamber 21 to the outer chamber over the top of the wall 25. A sample to be measured is caused to flow into the central chamber 21 through inlet tube 27, remotely controlled inlet valve 29 and a central passageway 31 extending through the bottom wall of the burette into the bottom of the central chamber 21. A tube 33 extends from the particle sensor 15 through the top wall of the burette down to near the bottom of the central chamber 21. The lower end of the tube 33 is spaced from the bottom of the central chamber 25 to allow fluid to flow from the central chamber 21 into the tube 33. The bottom of the central chamber 21 is conical to guide fluid to the center of the chamber 21 where the lower end of the tube 33 is located. The tube 33 connects to the sample inlet of the flow cell 13 of the particle sensor 15. The liquid sample, upon flowing from the central chamber 21 through the tube 33 and through the flow cell 13 of the sensor 15, then flows through an outlet tube 35 through a remotely controlled outlet valve 37 and through a flow control valve 39 to the sample outlet of the system.

In operation, the liquid sample will be first introduced to fill the central chamber 21 by opening the valve 29 and closing the valve 37. The sample is drawn into the central chamber 21 by a vacuum applied to the chambers 21 and 23. This action will fill the central chamber 21 and flush out the central chamber 21 eliminating any residue of a previous sample from the central chamber 21. When the central chamber 21 has been filled, it overflows and the sample flows to the floor of the outer chamber 23. A sonic sensor 45 detects the presence of the sample on the floor of the outer chamber 23 and generates a signal to indicate that the central chamber 21 is full. When the central chamber 21 is full, the valve 29 will be closed, the valve 37 will be opened, and pressure will be applied to the chambers 21 and 23 to force the sample in the central chamber 21 out through the tube 33, the particle sensor 15 and the outlet tube 35. As the sample within the central chamber is being forced out through the tube 33 and the sensor 15, the size of the particles in the sample are measured by the particle sensor 15 and pulse measuring system 18. At this time, the surface 22 of the sample will be moving downwardly within the central chamber 21. A sonic flow measuring system 47 is provided at the bottom wall of the central chamber 25 and continuously measures the distance between the surface of the sample within the central chamber 21 and the bottom of the chamber 21 and, by measuring the rate of downward displacement of this surface movement, the rate of flow of the sample through the sensor 15 is continuously monitored as the sample is being caused to flow through the particle sensor 15.

The sonic sensing system 47 measures the position of the surface of the sample within the central chamber 21 by repeatedly transmitting high frequency sonic pulses to the surface of the sample. These pulses are reflected back to a sonic pulse detector of the system 47 and the time for the pulse to travel to the surface and return provides a measurement of the distance between the surface of the sample and the bottom of the sample in accordance with the formula:

$$D=R_s t_s/2$$

wherein D is the distance from the bottom of the chamber to the liquid surface, $t_s$ is the time for the pulse to travel up and back between the bottom of the central chamber and the sample surface and $R_s$ is the rate of travel of sound in the sample. The time $t_s$ is determined by measuring the time interval between the transmission of the sonic pulse and the reception back of the sonic pulse reflected from the liquid surface and subtracting from this interval a constant T corresponding to the time for the sonic pulse to travel through the burette wall. The resulting difference will be $t_s$ representing the time travel of the sonic pulse up and back through the liquid sample.

The rate of sound travel $R_s$ through the liquid sample will vary for different samples and this fact must be taken into account to get an accurate measurement of the rate of flow through the sensor. When the liquid sample overflows the walls 25, as detected by the sensor 45, the sensing system 47 will automatically obtain a measurement of the time it takes the pulse to travel from the sensor to the surface of the sample and reflect back to the sensing system 47. This time measurement enables the system to take into account different rates of sound travel in different samples and obtain an accurate measurement of the position of the sample surface for samples having different rates of sonic transmission. a known value $D_o$. The known distance $D_o$ is related to. The distance between the liquid surface and the bottom of the chamber when the central chamber overflows is time of travel for the sonic pulse by the equation $D_o = R_s t_o/2$ in which $t_o$ is the time of travel of the sonic pulse up and back between the bottom of the central chamber and surface at the time of overflow. The time $t_o$ is determined by subtracting the constant T from the measured time interval of sonic pulse travel at the time of overflow. This time $t_o$ and the known distance between the surface of the fluid when the central chamber overflows and the bottom of the chamber 21 enables the distance between the surface of the liquid and the bottom of the chamber to be measured in accordance with the following equation:

$$D=(t_s/t_o) \times D_o$$

In this manner, an accurate measurement of the distance to the sample surface is obtained. By repeatedly measuring the surface position every 0.143 seconds, the rate of fluid flow through the sensor 15 can be continuously monitored regardless of variations in the rate of sound travel through the liquid sample.

As explained above, a vacuum is applied to the chambers 21 and 23 during the filling operation to initially draw the sample into the central chamber 21 through the inlet tube 27 and the valve 29. The vacuum is applied to the chambers 21 and 23 by a vacuum generator 41 through a normally open valve 43 during a "fill" step of the process. The vacuum generator is driven by pneumatic pressure applied from a source 49 of 60 to 100 psi gas pressure through pressure regulators 51 and 53, a remotely controlled valve 55 and a check valve 57. The valve 55 is normally closed and is energized to be open during the fill step of the measuring sequence so as to actuate the vacuum generator during the fill step. The pressure regulators 51 and 53 step the pressure applied to the vacuum generator down to 15 psi.

Following the fill step, the chambers 21 and 23 of the burette are pressurized during a "compress" step of the measuring process. In the compress step, the valve 43 is energized to close it and a normally closed valve 65 is energized to open it to apply pressure to the chambers 21 and 23 of the burette 11 from the high pressure source 49 through a pressure regulator 59, the valve 65 and a check valve 64. The regulator 59 steps the applied pressure down to a selected variable amount near 20 psi. When the chambers 21 and 23 have been pressurized, the "sample" step takes place in which the sample in the central chamber is forced through the particle sensor 15. During the sample step, the valve 43 will remain energized and closed, the valve 65 will remain energized and open to apply pressure to the chambers 21 and 23 and the valve 37 will be energized to open it. The pressure supplied by the regulator 59 to the burette 11 will force the sample in the central chamber 21 up through the tube 33 and the particle sensor 15 and out through the valve 37 to carry out the sample step of the sequence. During the sample step, the entrained particles are detected by the sensor 15 and measured. A gauge 67 is connected to the pressure line between the check valve 65 and the burette 11 to provide a measurement of the pressure within the burette 11. By manually varying the pressure supplied by the regulator 59, the pressure in the burette can be varied and thus the rate of sample flow from the central chamber 21 through the particle sensor 15 can be adjusted. By watching the rate of flow measurement provided by the sensor system 47, the rate of the sample flow can be readily adjusted to and maintained at a desired value as the sample is being caused to flow through the particle sensor 15.

The bottom of the outer chamber 23 is connected to the inlet side of the manual flow control valve 39 through a normally closed valve 69. The burette will normally be drained in a "drain" step following the sample step. This operation is carried out by energizing the valve 69 to open the valve 69 and, at the same time, energizing the valve 65 to apply pressure to the chambers 21 and 23. In addition, the normally open valve 43 is maintained energized to be closed. As a result, the pressure applied to the burette will force any fluid in the outer chamber 23 out through the valve 69 to the sample outlet.

The sequence of operation of the system is to start with the "vent" step wherein all of the valves 29, 37, 55, 65 and 69 will be de-energized and closed and the normally open valve 43 will be de-energized and open to vent the chambers 21 and 23 through the vacuum generator 41. The vacuum generator 41, however, at this time will not be operated due to the fact that the valve 55 is closed. The system returns to the vent step following the drain step whereupon the system is ready to receive and measure the next sample.

Before a new sample of a different chemical is measured, the system goes through a purge sequence which starts by alternately opening and closing the valve 65 while at the same time maintaining the valve 29 energized and open and the valve 43 de-energized and open. This action will purge the central chamber 25 and the inlet tube 27 of the previous sample. Following this cyclical energization of the valve 63, the valve 65 is energized simultaneously with the valve 37 so as to apply pressure through the tube 33, the sensor 15 and the tube 35 to purge fluid pressure on these parts of the system. Following this purge step, the valve 65 is energized simultaneously with the valve 69 to purge the drain line connecting through the valve 69.

Figure 3:
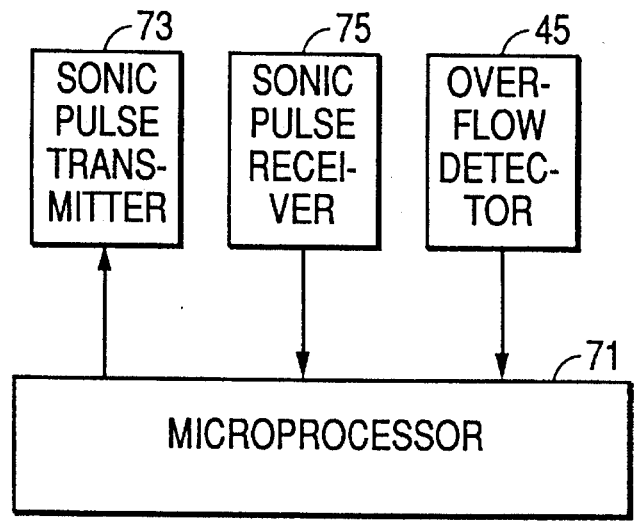
FIG. 3 illustrates the electronics of the flow rate measuring system.

As shown in FIG. 3, the electronics of the instrument comprises a microprocessor 71 which is connected to control sonic transmitter 73 of the flow sensor system 47. It is also connected to the receiver 75 of the sonic flow sensor as well as to the overflow sensor 45. In operation, the microprocessor 71 causes the transmitter 73 to transmit high frequency sonic pulses every five microseconds, measures the time interval from the time of transmission of the pulse to the receipt of a reflected pulse received by the receiver 73 and averages the measured time intervals over several cycles. From the measured average value, the position of the surface of the liquid in the central chamber is computed. This process is then repeated every .143 seconds or, in other words, once about every $\frac{1}{7}$th of a second. Each computed position is compared with the position of the surface in the previous computation to determine how far the surface traveled during the 0.143 second interval and from this difference, the flow rate is calculated and displayed. Thus, an instantaneous display of the flow rate is given to the operator of the system and from the displayed flow rate, the operator can adjust the regulator 59 to control the flow rate to be at the desired rate.

The above described measurements occur while the liquid in the central chamber 21 is being forced by the pressure in the burette up through the tube 33 and the particle sensor 15. Prior to this sample step, as described above, the sample will have been caused to fill the central chamber 21 and overflow the walls 25. This overflow is detected by the sensor 45 upon the liquid flowing over the sensor 45. The microprocessor 71, in response to receiving a signal from the overflow sensor 45, activates the sensor system 47 to measure the time of travel of the sonic pulses between the bottom of the central chamber 21 and the surface of the overflowing liquid. This sonic time travel is then stored for use in the flow rate computation during the sample step as described above.

In addition, the microprocessor computes the volume of flow during the sample step from the displacement of the surface of the sample as detected by the sensor system 47 and from the known effective cross sectional area of the central chamber 21. Thus, from the data provided by the pulse amplitude measuring system and the volume of flow during the sample step, the density of particles in each different size range can be determined.

Because the rate of flow during the sample step can be continuously monitored and adjusted to the desired value, the flow rate can be readily controlled without repeated trial and error steps to be at the desired rate to achieve an accurate and consistent measurement of particle sizes even though the samples have different viscosities.

The above description is of a preferred embodiment of the invention and modification may be made thereto without departing from the spirit and scope of the invention which is defined in the appended claims.

We claim:

1. A particle measuring system comprising means having a flow cell and operating to measure the size of particles entrained in liquid flowing through said flow cell, means defining a chamber for containing a liquid, wherein the liquid in said chamber defines a liquid surface in said chamber, flow providing means to provide a flow path between said chamber and said flow cell to cause liquid to flow between said chamber and said flow cell and through said flow cell at a rate of flow corresponding to the rate of vertical displacement of the surface of the liquid in said chamber, and means to continuously monitor the rate of flow of liquid through said flow cell by measuring the rate of vertical displacement of the surface of the liquid in said chamber.

2. A particle measuring system as recited in claim 1 further comprising means to control the rate of flow through said flow cell.

3. A particle measuring system as recited in claim 1, wherein said means to continuously monitor the rate of flow of liquid comprises means to reflect sonic pulses from said liquid surface in said chamber, and timing means to measure the time of travel of said sonic pulses to and from said liquid surface in said chamber.

4. A particle measuring system as recited in claim 3, wherein said means to reflect pulses from said liquid surface comprises means to transmit pulses through the liquid in said chamber to be reflected from said liquid surface back through the liquid in said chamber.

5. A particle measuring system as recited in claim 4, further comprising means to detect when said chamber is full, said timing means measuring the time of travel of pulses to and from said liquid surface in said chamber when said chamber is full, to provide data varying with the rate of transmission of sonic pulses in the liquid in said chamber, said means to measure the rate of displacement of said liquid surface of the liquid in said chamber determining the rate of displacement from the time of travel of sonic pulses measured by said timing means during said displacement and from said data to compensate for different rates of sonic transmission.

6. A particle measuring system as recited in claim 5, wherein said means to detect when said chamber is full detects the condition of said chamber being full by detecting that said chamber has overflowed.

7. A particle measuring system as recited in claim 1, wherein said means to cause liquid to flow between said chamber and said flow cell comprises a tube extending from said flow cell down through a top of said chamber to a point adjacent to a bottom of said chamber and means to apply pressure to said chamber to force the liquid in said chamber through said tube and said flow cell.

8. A method of measuring particle sizes entrained in liquid comprising the steps of filling a chamber with said liquid to form a liquid surface in said chamber, causing the liquid to flow from said chamber through a particle sensor while vertically displacing the liquid surface at a rate corresponding to the rate of flow through said particle sensor, measuring the rate of vertical displacement of the liquid surface in said chamber as said liquid is caused to flow from said chamber through said particle sensor, and adjusting the rate of flow through said sensor as indicated by said rate of displacement to a desired value.

9. A method as recited in claim 8, wherein the step of measuring the rate of displacement of said liquid surface is carried out by reflecting sonic pulses from said liquid surface and measuring the time of travel of said sonic pulses to and from said liquid surface.

10. A method as recited in claim 9, wherein said sonic pulses are transmitted through the liquid in said chamber to be reflected from said surface within the liquid in said chamber.

11. A method as recited in claim 10, wherein said step of filling said chamber includes filling said chamber until said chamber overflows and further comprising reflecting sonic pulses from the surface of the liquid in said chamber when said chamber overflows and measuring the time of travel of the sonic pulses through the liquid in said chamber when said chamber overflows.

\* \* \* \* \*

UNITED STATES PATENT AND TRADEMARK OFFICE
CERTIFICATE OF CORRECTION

PATENT NO. : 5,501,113
DATED : March 26, 1996
INVENTOR(S) : Charles Harrison et al.

It is certified that error appears in the above-indentified patent and that said Letters Patent is hereby corrected as shown below:

Column 3, line 58, delete "a known value $D_o$. The known Distance $D_o$ is related to";

line 60, after "overflows is", insert --a known value $D_o$. The known Distance $D_o$ is related to--.

Signed and Sealed this

Thirtieth Day of July, 1996

Attest:

BRUCE LEHMAN

Attesting Officer     Commissioner of Patents and Trademarks